(12) United States Patent
Oba (10) Patent No.: US 8,604,238 B2
(45) Date of Patent: Dec. 10, 2013

(54) METHOD FOR PRODUCING (METH) ACRYLIC ACID

(75) Inventor: Masaharu Oba, Himeji (JP)

(73) Assignee: Nippon Shokubai Co. Ltd. (JP)

( * ) Notice: Subject to any disclaimer, the term of this patent is extended or adjusted under 35 U.S.C. 154(b) by 545 days.

(21) Appl. No.: 12/521,684

(22) PCT Filed: Dec. 27, 2007

(86) PCT No.: PCT/JP2007/075212
§ 371 (c)(1),
(2), (4) Date: Jun. 29, 2009

(87) PCT Pub. No.: WO2008/081907
PCT Pub. Date: Jul. 10, 2008

(65) Prior Publication Data
US 2010/0286443 A1      Nov. 11, 2010

(30) Foreign Application Priority Data

Dec. 28, 2006   (JP) ................ 2006-355361
Dec. 28, 2006   (JP) ................ 2006-355386

(51) Int. Cl.
*C07C 57/02*   (2006.01)
*C07C 57/18*   (2006.01)

(52) U.S. Cl.
USPC ........................................... 562/598

(58) Field of Classification Search
None
See application file for complete search history.

(56) References Cited

U.S. PATENT DOCUMENTS

| 5,780,679 A | 7/1998 | Egly et al. |
| 6,667,419 B1 | 12/2003 | Matsumoto et al. |
| 6,825,381 B2 | 11/2004 | Hirao |
| 7,067,696 B2 | 6/2006 | Sakakura et al. |
| 7,183,428 B2 | 2/2007 | Ueno et al. |
| 7,258,766 B2 | 8/2007 | Yada et al. |
| 2004/0030185 A1* | 2/2004 | Hirao et al. ............... 562/547 |
| 2006/0211886 A1 | 9/2006 | Yada et al. |

FOREIGN PATENT DOCUMENTS

| JP | 2003-206256 | 7/2003 |
| JP | 2004-067616 | 3/2004 |

* cited by examiner

*Primary Examiner* — Johann R Richter
*Assistant Examiner* — Jennifer C Sawyer
(74) *Attorney, Agent, or Firm* — Fox Rothschild LLP; Peter J. Butch, III; Wansheng Jerry Liu (57) ABSTRACT

A method for producing (meth)acrylic acid relevant to the present invention has the step for producing (meth)acrylic acid-containing gas by subjecting raw material gas to a catalytic vapor phase oxidation reaction in a reactor for catalytic vapor phase oxidation; and the step for obtaining a (meth)acrylic acid solution by introducing (meth)acrylic acid-containing gas thus produced to an absorption tower and separating non-condensable gas from (meth)acrylic acid-containing gas, and it is an object to provide a method for obtaining a high concentration acrylic acid solution stably by controlling temperature of (meth)acrylic acid-containing gas just before being supplied to the absorption tower, regardless of temperature fluctuation of gas discharged from the reactor for catalytic vapor phase oxidation.

15 Claims, 3 Drawing Sheets

METHOD FOR PRODUCING (METH)ACRYLIC ACID

CROSS REFERENCE TO RELATED APPLICATION

The present application is a 35 U.S.C. §371 National Phase application of International Application Serial No. PCT/JP07/75212 filed Dec. 27, 2007, which claims priority under the Paris Convention to Japanese Patent Application Serial Nos. 2006-355361 and 2006-355386, both filed Dec. 28, 2006. The disclosures of all three applications are incorporated herein by reference in their entirety.

TECHNICAL FIELD

The present invention relates to a method for producing (meth)acrylic acid. More specifically, the present invention relates to a method for producing (meth)acrylic acid having the step for obtaining (meth)acrylic acid-containing gas by subjecting a raw material for (meth)acrylic acid to catalytic vapor phase oxidation by molecular oxygen-containing gas, and the step for carrying out temperature control of this (meth)acrylic acid-containing gas; and then the step for obtaining a (meth)acrylic acid solution having high concentration by introducing the gas to an absorption tower and contacting with an absorbing agent for acrylic acid, and separating non-condensable gas.

BACKGROUND ART

Acrylic acid or methacrylic acid (hereafter they are referred to as "(meth)acrylic acid" collectively) is one used as a production raw material of industrial products, and a chemical substance mass produced in a large scale plant. In general, these compounds are produced via the step for obtaining a solution of (meth)acrylic acid by separation of non-condensable gas from a crude product, or further by the various purification steps, to obtain high purity products.

For example, in the step for producing acrylic acid, propylene, propane, acrolein or the like is subjected to catalytic vapor phase oxidation by molecular oxygen-containing gas in the presence of an oxidation catalyst, by which byproducts of substances with low boiling point are generated, such as acetic acid, lower aldehyde, water and the like; and substances with high boiling point such as furfural, maleic anhydride and the like, other than acrylic acid which is an objective product. Therefore, the product is obtained by introducing the resulting mixed gas to a separation apparatus (for example, an absorption tower) of non-condensable gas, and by subjecting to condensation or contacting with an absorbing agent for acrylic acid to obtain a solution containing acrylic acid and other byproducts, and by separation and purification of acrylic acid from this solution by a method such as distillation, diffusion, extraction, crystallization or the like.

In this way, as a method for producing (meth)acrylic acid having the step for obtaining a (meth)acrylic acid solution by introducing (meth)acrylic acid-containing gas obtained by catalytic vapor phase oxidation of propylene etc. to a separation apparatus (absorption tower), and subjecting the gas to contact with an absorbing agent for acrylic acid, there are for example, technologies disclosed in (A) U.S. Pat. No. 7,067,696B2, (B) US2006/0211886A1, (C) U.S. Pat. No. 6,667,419B2, (D) U.S. Pat. No. 5,780,679A, (E) U.S. Pat. No. 7,258,766B2, (F) U.S. Pat. No. 6,825,381B2 and (G) U.S. Pat. No. 7,183,428B2. In these Patent Literatures, it is described that (meth)acrylic acid-containing gas is cooled before being supplied to a capturing tower, which is a kind of a separation apparatus of non-condensable gas. For example, in Patent Literature (C), it is described that (meth)acrylic acid-containing gas comes out from a reactor at from 200 to 350° C., and supplied to an absorption tower, which is a kind of a separation apparatus of non-condensable gas, at from 100 to 300° C.

These methods have each characteristics, in such a way that as for technology of Patent Literature (A), temperature of mixed gas at the suction port of an compressor is specified, to suppress clogging or the like of the compressor of molecular oxygen-containing gas to be used in a catalytic vapor phase oxidation reaction. As for technologies of Patent Literatures (B) and (C), as they are for suppressing clogging of a separation apparatus of non-condensable gas, a method in which (meth)acrylic acid-containing gas is supplied from a plurality of places to a separation apparatus, and a method in which filling substances with different absorption efficiency are set inside a separation apparatus in multiple stages, respectively, are disclosed.

In addition, as for technology of Patent literature (D), energy is removed from a separation apparatus of non-condensable gas in order to solve a problem of entrainment of acrylic acid by discharged gas. Also as for technology of Patent literature (E), mass fraction of acrylic acid in acrylic acid-containing gas is specified in order to reduce concentration of acrylic acid remained in discharged gas.

However, in these technologies, there is no consideration on fluctuation of concentration of a (meth)acrylic acid solution obtained from a separation apparatus of non-condensable gas. On the other hand, there is technology described in Patent Literature (F), as technology for controlling concentration of a (meth)acrylic acid solution, in view of the fact that fluctuation of an amount of water contained in a (meth)acrylic acid solution makes difficult to secure operation service stability in the next and the subsequent steps. Such technology has been proposed in considering the fact that variation of the amount of water contained in gas discharged from a reactor, depending on fluctuation of atmosphere condition, results in fluctuation of concentration of a (meth)acrylic acid solution, and is technology to control concentration of (meth)acrylic acid by changing the amount of water in gas discharged from the tower top by means of controlling temperature or pressure at the tower top of a capturing tower. However, in this literature, there is no disclosure on relation between the temperature of gas discharged from a reactor, and the concentration of the acrylic acid solution.

In addition, a high concentration of a (meth)acrylic acid solution obtained from a separation apparatus of non-condensable gas, enhances efficiency in the following purification step. Therefore, technology to increase the concentration has also been developed. Patent Literature (G) discloses technology for subjecting an acrylic acid solution obtained in the capturing tower to the crystallization step and the distillation step, and then subjecting the resulting distillate to circulate into the capturing tower. By such technology, an acrylic acid solution with a high concentration of equal to or higher than 80% by volume can be obtained. However, although an acrylic acid solution with high concentration can be obtained according to the technology, the technology is not aimed at obtaining an acrylic acid solution in constant concentration stably.

As described above, technology to capture (meth)acrylic acid efficiently by separation of non-condensable gas from (meth)acrylic acid-containing gas, which is obtained by a catalytic vapor phase oxidation reaction, has been known conventionally. However, it was found that these prior arts raised a problem when they are applied to obtaining a (meth) acrylic acid solution with high concentration stably from a separation apparatus of non-condensable gas.

Namely, as described also in prior arts, temperature range of (meth)acrylic acid-containing gas obtained by a catalytic vapor phase oxidation reaction is, for example, from 200 to 350° C., which exceeds 100° C. This is because, although the reaction proceeds even at low temperature as long as a catalyst to be used maintains sufficient activity, the reaction temperature is forced to be raised to maintain production amount of (meth)acrylic acid in response to deterioration of the catalyst, resulting in increase in also temperature of the resulting (meth)acrylic acid-containing gas. In addition, in the step for obtaining a (meth)acrylic acid solution by separation of non-condensable gas from (meth)acrylic acid-containing gas, compounds having low boiling point, such as water and the like continue to evaporate. Therefore, in response to temperature or water content of the (meth)acrylic acid-containing gas, concentration of the resulting (meth)acrylic acid solution fluctuates. To solve this problem, in general, such measures are taken that the concentration of a (meth)acrylic acid solution is maintained constant by controlling temperature of the separation apparatus, by using a method that, for example, a part of the resulting (meth)acrylic acid solution is circulated to a separation apparatus of non-condensable gas (an absorption tower), and the amount of the circulation solution to pass through a cooler installed at a circulation line or the like is controlled before the circulation solution is circulated to the separation apparatus.

Here, although it is manageable even by this embodiment in order to obtain a (meth)acrylic acid solution having concentration required conventionally, however, there were not-manageable cases in obtaining a solution having high concentration. For example, conventionally, concentration of a (meth)acrylic acid solution obtained from a separation apparatus of non-condensable gas (an absorption tower) is in a degree of from 50 to 70% by mass. In this case, because amount of steam discharged from the separation apparatus of non-condensable gas is low, and it is enough to actively cool the separation apparatus of non-condensable gas, control can be carried out easily. However, in the case where an object is to obtain a (meth)acrylic acid solution with higher concentration, subtle control is required in response to temperature variation of (meth)acrylic acid-containing gas which is introduced into the separation apparatus of non-condensable gas, which results in out of a controllable range by the separation apparatus of non-condensable gas, or forced to operate at the vicinity of limit of the controllable range, thus giving fluctuation of concentration of a (meth)acrylic acid solution, even by a very small external turbulence.

In more specifically, in the case of obtaining a (meth) acrylic acid solution having conventional concentration, provided that minimal heat removal amount in a (meth)acrylic acid solution to be circulated is 100, a maximal heat removal amount of about 150 may be enough. However, in the case of obtaining a (meth)acrylic acid solution having high concentration, because it is required to maintain temperature inside a separation apparatus relatively high to increase amount of water to be evaporated inside the separation apparatus of non-condensable gas, and extremely small amount of heat removal is necessary when gas temperature at the entrance is low, heat removal amount of a solution to be circulated is set to be about 26 to 140. Difference of heat removal amount in this case is about 5.4 times (140/26) as compared with a conventional case of 1.5 times (150/100), thus resulting in out of a controllable range by a method such as controlling amount of circulating solution passing through a cooler at the circulation line, which inevitably provides concentration fluctuation. On the other hand, in order to obtain more concentrated (meth)acrylic acid solution, the water discharge amount is necessary to be increased by means of increasing the temperature inside acrylic acid absorption tower or by decreasing the pressure, for example. For the means, simply temperature of the acrylic acid absorption tower can be set high. If high concentrated (meth)acrylic acid solution is aimed in the case of low temperature of the gas including (meth)acrylic acid, the heat removal amount in the acrylic acid absorption tower should be decreased. However, the conventional systems have only a means to cool the acrylic acid absorption tower to effectively capture (meth)acrylic acid. Then, in the case of low temperature of the gas including (meth)acrylic acid, the conventional systems have not been able to control the temperature of the separation apparatus of non-condensable gas by removing slight amount of heat to obtain (meth)acrylic acid solution as high concentrated as the case of high temperature. Namely, it is impossible to obtain a (meth)acrylic acid solution having high concentration stably by a conventional method.

Accordingly, it is an object of the present invention to provide a method for obtaining an acrylic acid solution having high concentration stably, regardless of temperature fluctuation of gas discharged from a reactor for catalytic vapor phase oxidation, in the step for producing (meth)acrylic acid by a catalytic vapor phase oxidation reaction.

DISCLOSURE OF THE INVENTION

The present inventors have intensively studied condition to stably provide high concentration and constant concentration of a (meth)acrylic acid solution obtained from a separation apparatus of non-condensable gas (an absorption tower) regardless of temperature of (meth)acrylic acid-containing gas. As a result, it was found that the problem could be easily solved by suitably adjusting temperature of (meth)acrylic acid-containing gas, obtained by a catalytic vapor phase oxidation reaction, while conventionally cooling was carried out on (meth)acrylic acid-containing gas, by a simple waste heat recovery type heat exchanger or cooler or the like, in a degree of only heat amount comparable to heat conduction capability thereof, before supplying to a separation apparatus of non-condensable gas, and have thus completed the present invention.

In addition to the above-mentioned findings, the inventors completed the present invention by discovering that providing a heating means in the acrylic acid absorption tower enables to maintain the heat removing controllability of acrylic acid absorption tower and to constantly yield high concentrated (meth)acrylic acid solution even if the temperature of the gas including (meth)acrylic acid is low.

Namely the above objectives can be attained by the following (1) to (12):

(1) A method for producing (meth)acrylic acid comprising: the step (1) for producing (meth)acrylic acid-containing gas over a long period by subjecting a raw material for (meth) acrylic acid to catalytic vapor phase oxidation by molecular oxygen-containing gas, in the presence of an oxidation catalyst; then
the step (2) for cooling said (meth)acrylic acid-containing gas; and then
the step (3) for obtaining a (meth)acrylic acid solution by introducing said cooled gas to an absorption tower and contacting with an absorbing agent for acrylic acid to separate non-condensable gas, characterized in that the (meth)acrylic acid solution with a high concentration of equal to or higher than 75% by mass is obtained, by setting lower limit of cooling temperature in the step (2) for cooling said (meth)acrylic acid-containing gas, from operation condition of the step (3) for obtaining the (meth)acrylic acid solution, and controlling cooling of said gas during whole reaction period so that said gas does not become below said lower limit of cooling temperature.

(2) The method according to the above (1), wherein the temperature control is carried out by controlling heat removal amount of the (meth)acrylic acid-containing gas supplied to the absorption tower, in response to temperature of the (meth)acrylic acid-containing gas obtained by a catalytic vapor phase oxidation reaction.

(3) The method according to the above (2), wherein the means of the temperature control of the gas is installed between a catalytic vapor phase reactor and the absorption tower.

(4) The method according to any one of the above (1) to (3), wherein temperature of the (meth)acrylic acid-containing gas to be supplied to the absorption tower is controlled at from 200 to 300° C.

(5) The method according to any one of the above (1) to (3), wherein temperature of the (meth)acrylic acid-containing gas to be supplied to the absorption tower is controlled at from 210 to 290° C.

(6) The method according to any one of the above (1) to (3), wherein temperature of the (meth)acrylic acid-containing gas to be supplied to the absorption tower is controlled at from 230 to 280° C.

(7) The method according to any one of the above (1) to (6), wherein temperature fluctuation range of the (meth)acrylic acid-containing gas to be supplied to the absorption tower is controlled within 40° C.

(8) The method according to any one of the above (1) to (7), wherein temperature fluctuation range of the (meth)acrylic acid-containing gas to be supplied to the absorption tower is controlled within 30° C.

(9) The method according to any one of the above (1) to (7), wherein fluctuation range between maximal value and minimal value of concentration of (meth)acrylic acid in the (meth) acrylic acid solution to be taken out from the tower bottom of the absorption tower is ±2%.

(10) The method according to any one of the above (1) to (8), wherein water concentration of a (meth)acrylic acid solution to be discharged from the absorption tower is set from 1 to 10% by mass.

(11) The method for producing (meth)acrylic acid according to any one of the above (1) to (10), wherein temperature of the (meth)acrylic acid-containing gas supplying to the absorption tower is controlled by any of a gas temperature control unit shown below:
(1) a waste heat recovery type heat exchanger in which temperature of (meth)acrylic acid-containing gas is controlled by changing supply amount of (meth)acrylic acid-containing gas passing through inside,
(2) a waste heat recovery type heat exchanger for carrying out heat exchange by generation of steam, in which temperature of (meth)acrylic acid-containing gas is controlled by changing pressure of steam,
(3) a waste heat recovery type heat exchanger for carrying out heat exchange by generation of steam, in which temperature of (meth)acrylic acid-containing gas is controlled by changing liquid surface level of liquid inside to be evaporated, and
(4) a waste heat recovery type heat exchanger for carrying out heat exchange by passing a cooling medium, in which temperature of (meth)acrylic acid-containing gas is controlled by changing flow rate of the cooling medium.

(12) The method for producing (meth)acrylic acid according to any one of the above (1) to (11), wherein a (meth) acrylic acid solution with a high concentration of equal to or higher than 75% by mass is obtained, by heating and cooling the tower bottom solution of the absorption tower, and re-circulating to the absorption tower, in the step (3) for obtaining a (meth)acrylic acid solution by introducing the cooled gas to the absorption tower and contacting with an absorbing agent for acrylic acid and separating non-condensable gas.

BEST MODE FOR CARRYING OUT THE INVENTION

A method for producing (meth)acrylic acid according to the present invention is composed of:
the step (1) for producing (meth)acrylic acid-containing gas over a long period by subjecting a raw material for (meth) acrylic acid to catalytic vapor phase oxidation by molecular oxygen-containing gas, in the presence of an oxidation catalyst; then
the step (2) for cooling said (meth)acrylic acid-containing gas; and then
the step (3) for obtaining a (meth)acrylic acid solution by introducing said cooled gas to an absorption tower and contacting with an absorbing agent for acrylic acid to separate non-condensable gas,
characterized in that the (meth)acrylic acid solution with a high concentration of equal to or higher than 75% by mass is obtained, by setting lower limit of cooling temperature in the step (2) for cooling said (meth)acrylic acid-containing gas, from operation condition of the step (3) for obtaining the (meth)acrylic acid solution, and controlling cooling of said gas during whole reaction period so that said gas does not become below said lower limit of cooling temperature.

First of all, explanation will be given on a catalytic vapor phase oxidation reaction using production of acrylic acid as a representative example. Those skilled in the art can make such application, with reference to the following explanation, that as for methacrylic acid, for example, methacrolein is used instead of acrolein as a raw material.

By using propylene, propane, acrolein or the like as a raw material of the reaction, and supplying those to a reactor for catalytic vapor phase oxidation filled with an oxidation catalyst, together with inert gas or the like and molecular oxygen-containing gas such as air or the like, whose pressure is raised by a blower, acrylic acid-containing gas is generated by subjecting those to a catalytic vapor phase oxidation reaction.

Here as a reactor to be used for a catalytic vapor phase oxidation reaction, it is not especially limited, as long as one generating acrylic acid in the presence of a catalyst for catalytic vapor phase oxidation, however, it is preferable to utilize a multi-tube type reactor in view of excellent reaction efficiency. Specifically, a catalytic vapor phase oxidation reaction is carried out by using a reactor of a multi-tube type reactor or the like, and supplying predetermined amount of reaction raw material gas composed of raw material components such as propylene, propane, acrolein and the like, inert gas or the like, and molecular oxygen-containing gas such as air or the like, in the presence of an oxidation catalyst. Here when propylene is used as a raw material component, acrolein is first generated, and by subjecting this to further catalytic vapor phase oxidation, acrylic acid is obtained. As the reaction step adopted in the present invention, it is no object whether it is one-stage method where these reactions are carried out in one reactor, or two-stage method where these reactions are carried out in different reactors. In addition, as for reaction condition such as an oxidation catalyst to be used, along with raw material components, gas concentration of molecular oxygen, inert gas or the like, reaction temperature or the like, any of conventionally known condition for the reaction step for generating acrylic acid can be applied.

For example, as for the raw material components, any of propylene, propane, acrolein or a mixture of two or more kinds thereof can be used, and it is suitable that these raw material components are from 6 to 20% by volume, preferably from 8 to 15% by volume, based on reaction raw material gas to supply into a reactor. In addition, in order to be subjected to an oxidation reaction, this reaction raw material gas contains molecular oxygen in 1 to 3 times (molar ratio) raw material components, and the remaining is inert gas such as nitrogen, carbon dioxide, steam or the like.

In addition, for example, in order to produce acrylic acid in the present invention by subjecting propylene-containing gas to a catalytic vapor phase oxidation reaction, as a catalyst to be used in the former stage reaction to generate acrolein by catalytic vapor phase oxidation of propylene, an oxidation catalyst generally used to produce acrolein, by catalytic vapor phase oxidation of raw material gas containing propylene, can be used. Similarly, as for a catalyst to be used in the later stage reaction to generate acrylic acid, by catalytic vapor phase oxidation of acrolein obtained in the former stage reaction, it is not especially limited, and an oxidation catalyst generally used to produce acrylic acid, by catalytic vapor phase oxidation of reaction gas containing acrolein, can be used.

In acrylic acid-containing gas obtained by this catalytic vapor phase oxidation reaction, acrylic acid, molecular oxygen, unreacted raw material components, inert gas are contained, and other by-produced impurities, such as water, acetic acid, propionic acid, maleic acid, acetone, acrolein, furfural, formaldehyde and the like, are contained.

In the reaction, it is necessary to raise reaction temperature in response to time deterioration of a catalyst, to maintain production amount of (meth)acrylic acid. In addition, reaction temperature differs depending on a catalyst to be used. Therefore, temperature of (meth)acrylic acid-containing gas, discharged from a reactor, generally has a range of from 200 to 350° C., that is over 100° C. In addition gas discharged from the reactor is conventionally cooled to about 100 to 300° C. as appropriate, before being supplied to a separation apparatus of non-condensable gas (an absorption tower), and as a heat exchanger to be used in such cooling, a waste heat recovery type heat exchanger such as one generating steam with constant pressure or the like is used to carry out heat removal depending on only heat conduction capability of the heat exchanger. However, because such a waste heat recovery type heat exchanger can provide heat removal amount only comparable to heat conduction capability of the heat exchanger, temperature of reaction gas after cooling results in to have a large temperature fluctuation range of equal to or larger than 100° C., depending on temperature fluctuation of gas discharged from the reactor.

A method of the present invention is technique to obtain the solution stably, regardless of setting concentration of (meth)acrylic acid in a (meth)acrylic acid solution to be taken out of the tower bottom of a separation apparatus of non-condensable gas (an absorption tower), as high as equal to or higher than 75% by mass, preferably from 80 to 98% by mass and more preferably from 85 to 98% by mass. Although a (meth)acrylic acid solution discharged from the separation apparatus of non-condensable gas is supplied to the purification step such as the step of distillation, diffusion, extraction or crystallization or the like for separating impurities, by setting concentration thereof as high as equal to or higher than 75% by mass, it becomes easier to use the crystallization step, which is simpler and more convenient operation as compared with the step of distillation, diffusion, or extraction. In addition, because the solution can be subjected to the crystallization step as it is, without subjecting to the dehydration step such as the distillation step or the like, purification of (meth)acrylic acid becomes much more efficient. In this way, by setting concentration of (meth)acrylic acid to be 75% by mass, facility cost and utility cost in the next and the subsequent steps can be reduced. In addition, amount of waste water can be reduced also. More suitably, the concentration is set to be equal to or higher than 80% by mass. On the other hand, because it is substantially difficult to make concentration of (meth)acrylic acid over 98% by mass, it is preferable to set upper limit to be 98% by mass.

The producing method for (meth)acrylic acid by the present invention controls the temperature of the gas including (meth)acrylic acid obtained through catalytic vapor phase oxidation reaction. That is, it is the most important feature that the lower limit of cooling temperature in the step (2) of cooling the gas including (meth)acrylic acid is predetermined from the operation conditions in the step (3) of yielding (meth)acrylic acid solution and that the gas cooling is controlled so as not to underrun the lower limit of cooling temperature through the whole reaction period. The working of the present invention is described in detail below.

If the acrylic acid concentration of the tower bottom liquid in acrylic acid absorption tower is 90 mass % for example, the operation temperature of the absorption tower (the temperatures of tower top and tower bottom) is derived from the flow volume of feed, bottom and top in the acrylic acid absorption tower and the operation pressure determined. Also, when knowing the minimum cooling amount which can be controlled in cooling the circulating liquid at the absorption tower bottom, the lower limit of the outlet temperature (gas concentration at the inlet of absorption tower) from the waste heat recovery type heat exchanger in front of the absorption tower can be determined. When falling below the lower limit, the control of cooling in the absorption tower is disturbed, then the concentration of acrylic acid aqueous solution (tower bottom liquid) widely varies. In addition, when decreasing the outlet temperature from the waste heat recovery type heat exchanger, the operation temperature of the absorption tower even if the absorption tower is not cooled, and therefore, the concentration of acrylic acid aqueous solution (tower bottom liquid) diminishes. In other words, the water concentration in the acrylic acid aqueous solution increases.

The present invention was achieved to solve the above-mentioned problems. In the prior art, it has been enough to absorb acrylic acid with high yield, that is, it has been understood that the lower cooling temperature is, the more advantageous. Consequently, the idea that the lower limit of the cooling temperature through the step (2) of cooling the gas including (meth)acrylic acid is controlled to be within a suitable temperature range has never been raised.

In the present invention, for example, in response to temperature of the resulting (meth)acrylic acid-containing gas, heat removal amount of the gas before being supplied to an absorption tower is controlled. Namely, different from a conventional technology, where cooling is carried out by heat removal amount depending only to heat conduction capability of a heat exchanger of (meth)acrylic acid-containing gas, or heat removal is not carried out, in the present invention, in response to deterioration of a catalyst, namely increase in temperature of (meth)acrylic acid-containing gas, temperature thereof is controlled. Therefore, in the case of obtaining a (meth)acrylic acid solution having particularly high concentration, according to a conventional method such as by controlling amount of a circulating solution passing through a cooler installed at a circulation line, to make temperature of a separation apparatus (an absorption tower) constant, it results in out of a controllable range of heat removable amount, and concentration fluctuation of a solution is inevitably generated, however, in the present invention, a solution having high concentration can be stably obtained by using a similar method. Therefore, not only facility cost and utility cost in the purification steps such as distillation, diffusion, extraction, crystallization or the like, to separate impurities contained in a (meth)acrylic acid solution, can be reduced, but also waste water amount can be reduced.

Temperature of (meth)acrylic acid-containing gas is controlled by heat removal control of an absorption tower so that concentration of a (meth)acrylic acid solution obtained by a separation apparatus of non-condensable gas becomes nearly constant at high concentration. In general, higher temperature of an absorption tower increases water content discharged with non-condensable gas, and increases concentration of a (meth)acrylic acid solution. Therefore, because in the case where a catalyst has sufficient activity and a reaction proceeds even at low temperature, temperature of the resulting (meth) acrylic acid-containing gas also becomes low, heat removal amount of gas should be reduced to make concentration of a (meth)acrylic acid solution high. On the other hand, because in the case where production amount of (meth)acrylic acid cannot be maintained if reaction temperature is not high, caused by deterioration of a catalyst, temperature of (meth) acrylic acid-containing gas also becomes high, heat removal amount of gas should be increased. In the present invention, to obtain a (meth)acrylic acid solution having high concentration, gas temperature is controlled so that temperature of gas at the entrance of a separation apparatus becomes not too low. In particular, by decreasing heat removal amount when gas temperature is low, (meth)acrylic acid-containing gas is supplied as it is, in a high temperature state, to an absorption tower. In this way, difference in heat removal amount, caused by a conventional temperature control method in the absorption tower, becomes small, and temperature control by this method becomes possible, and a (meth)acrylic acid solution having high concentration can be stably obtained. More preferably, in the present invention, means to heat and cool the tower bottom liquid are provided in the acrylic acid absorption tower, thereby the tower bottom liquid is heated and then cooled (or heated and then cooled) and the temperature is controlled, thereafter the liquid circulates in the acrylic acid absorption tower. The means to heat and cool may be each independent device or may be one device having both functions, so long as at least a portion of the tower bottom liquid can be necessarily heated. Thereby, high concentrated (meth) acrylic acid solution is constantly yielded. Conventionally, the tower does not have a heating means and the temperature of the tower bottom liquid is controlled only by a cooling means, resulting in that high concentrated (meth)acrylic acid solution cannot be constantly obtained as above described.

It is desirable that a temperature of (meth)acrylic acid-containing gas, supplied to an absorption tower, is preferably controlled at from 200 to 300° C., more preferably from 210 to 290° C., and further preferably from 230 to 280° C. By setting the temperature at equal to or higher than 200° C., suppression of condensation of components, having lower boiling point than that of acrylic acid, can be furthermore enhanced, and temperature control of the absorption tower to make a (meth)acrylic acid solution high concentration becomes possible. On the other hand, by setting the temperature at equal to or lower than 300° C., cooling load in the absorption tower can be reduced, and production efficiency of (meth)acrylic acid can be further more enhanced.

In the above method for production, to make concentration of (meth)acrylic acid in a (meth)acrylic acid solution to be taken out of the tower bottom of an absorption tower "nearly the same" may be a range not necessary to vary condition of the subsequent purification step or the like, and for example, means to set an fluctuation range between maximal value and minimal value of the concentration within ±2%. Because smaller value of the fluctuation range is better, it is more preferably within ±1%, and most preferably 0%. By setting the fluctuation range within ±2%, fluctuation of condition in the next purification step can be furthermore suppressed. As a result, load or work to set or vary operation condition in response to concentration of (meth)acrylic acid in the next and the subsequent steps such as the purification and the like, can be furthermore reduced, and (meth)acrylic acid can be produced further more stably.

A temperature fluctuation of (meth)acrylic acid-containing gas to be supplied to the absorption tower is preferably controlled within 40° C. It is because a (meth)acrylic acid solution having high concentration can be produced further more stably. More suitably the temperature fluctuation is controlled within 30° C.

Further, a water concentration of a (meth)acrylic acid solution to be taken out of the bottom of the absorption tower is not especially limited, however, it is preferably set to be from 1 to 10% by mass. It is because, by setting the water content to be equal to or lower than 10% by mass, water can be separated sufficiently, concentration of (meth)acrylic acid can be increased relatively, and purification of (meth)acrylic acid in the next and subsequent steps becomes further more efficient. On the other hand, because it is substantially impossible to make the water concentration below 1% by mass, it is preferable to set lower limit to be 1% by mass.

The (meth)acrylic acid-containing gas adjusted to have a constant temperature range by controlled heat removal, is then supplied to an absorption tower, where non-condensable gas is separated by a capturing agent or by condensation to provide a (meth)acrylic acid solution. Here, "non-condensable gas" means one showing a gas state at normal temperature and normal pressure, and for example, includes propylene, propane, carbon dioxide, carbon monoxide, nitrogen, oxygen or the like. In addition, as for water or the like contained in (meth)acrylic acid-containing gas, a ratio of one contained in a (meth)acrylic acid solution, and one discharged with non-condensable gas is determined depending mainly on temperature of gas discharged from a separation apparatus of non-condensable gas. Because such a ratio has big influence on concentration of a (meth)acrylic acid solution, by controlling temperature of (meth)acrylic acid-containing gas to be supplied to a capturing tower, temperature control of a separation apparatus of non-condensable gas becomes easy, in obtaining a (meth)acrylic acid solution having high concentration, and concentration of a (meth)acrylic acid solution can be made nearly constant at high concentration.

Here, in the case where an absorption tower is such a type for absorbing (meth)acrylic acid by a capturing agent, a conventionally known absorption tower can be used. It is not especially limited, as long as one, for example, that can supply (meth)acrylic acid-containing gas from the lower part, supply a capturing agent, for example, water from the upper part, subject reaction gas to contact with the capturing agent in the tower, discharge non-condensable gas from the tower top part and discharge a condensed solution from the tower bottom.

The capturing agent to be used is not especially limited, and includes for example, one having water as a main component. In addition, as a solution having water as a main component, it is economical and preferable to recover and reuse a part of or whole amount of waste water generating in the production step of (meth)acrylic acid, and a waste solution generating in the next step, namely the purification step of (meth)acrylic acid or the like. In addition, depending on the cases, a waste solution in washing may be used by mixing.

Here, as a method for contacting (meth)acrylic acid-containing gas with the capturing agent, known methods for contacting can be used, and for example, cross-flow contact by using a bubble cap tray, a uni-flux tray, a sieve tray, a jet tray, a valve tray, a venturi tray, and any of an arbitrary combination thereof; counter flow contact by using a turbo grid tray, a dual flow tray, a ripple tray, a Kittel tray, an irregular filler, a regular filler, and any of an arbitrary combination thereof; and the like are included. Among these, a method for contacting (meth)acrylic acid-containing gas with the capturing agent by counter flow contact is advantageous, and in particular, it is advantageous to install fillers with high absorption efficiency at the upstream side in flow of the capturing solvent inside the tower, and fillers with relatively low polymerization generation capability and/or plate (tray) at the downstream side. In addition, as for supply temperature or supply amount of the capturing solvent, it can be set as appropriate.

As described above, kind of an absorption tower to be used in the present invention is not especially limited, however, it is more suitable to use one using a capturing agent, namely, a capturing tower.

As for a temperature at the discharge part of an absorption tower for non-condensable gas, for example, at the tower top of an absorption tower, it is not especially limited, and a conventionally known temperature range may be used, however, it is preferable to be in a range of from 40 to 80° C. It is because the temperature below 40° C. increases not only facility cost and utility cost for cooling, but also increases condensation of substances having lower boiling point than that of (meth)acrylic acid, incurring lowering of concentration of (meth)acrylic acid in a (meth)acrylic acid solution obtained from a separation apparatus of non-condensable gas, and also increasing waste water amount. In addition, the temperature over 80° C. is not preferable because loss of (meth)acrylic acid from the discharge part of non-condensable gas of a separation apparatus of non-condensable gas increases, which provides cost increase of a product of (meth)acrylic acid.

Also as for pressure at the discharge part of non-condensable gas of an absorption tower, a conventionally known pressure range can be adopted, and it is not especially limited, however, it is preferable to be a range of from 0 to 30 kPa (gauge pressure). It is because the pressure lower than 0 kPa (gauge pressure) requires a depressurization apparatus, and thus increases facility cost and utility cost, while the pressure over 30 kPa (gauge pressure) requires a large scale blower for supplying raw material gas to a reactor for catalytic vapor phase oxidation, and thus increases facility cost and utility cost, and not economical.

In addition, non-condensable gas discharged from an absorption tower may be treated as a whole as discharged gas, however, it is advantageous that a part thereof is circulated, as recycle gas, to a reactor by using, for example, a blower, because supply amount of inert gas or the like can be reduced.

Figure 2:
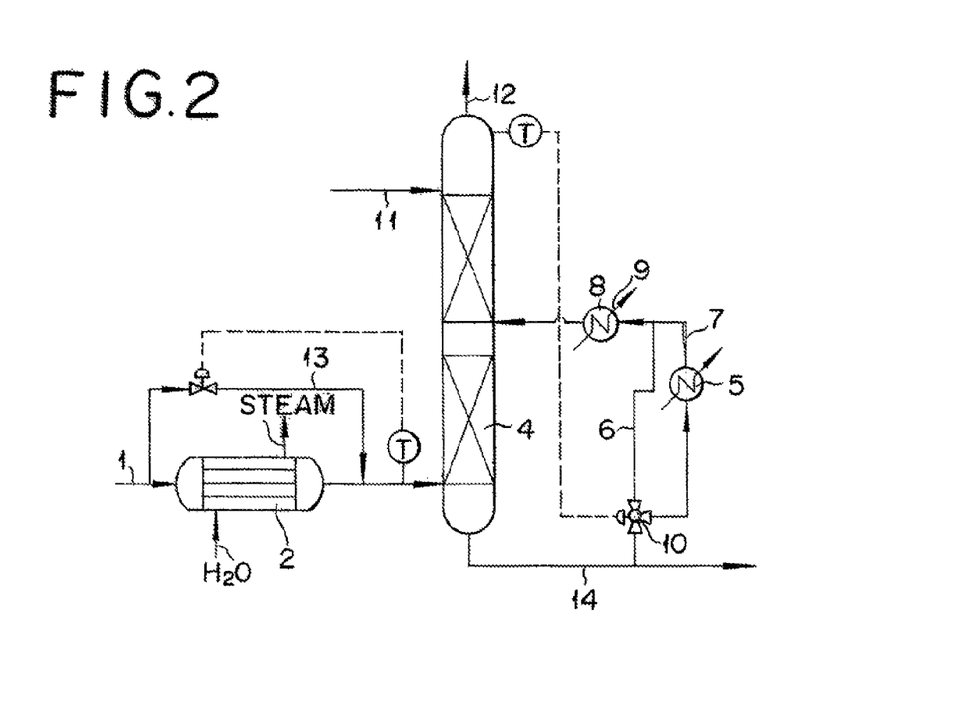
FIG. 2 a flow sheet showing an example of a method for producing (meth)acrylic acid according to the present invention.

As a method for controlling temperature of (meth)acrylic acid-containing gas, just before being supplied to an absorption tower, namely at the entrance part of the absorption tower 4, the following methods (1) to (5) are included:

(1) A waste heat recovery type heat exchanger 2, where temperature of (meth)acrylic acid-containing gas is controlled by varying a supply amount of (meth)acrylic acid-containing gas, passing through inside (FIG. 2). Variation of the supply amount can be carried out, for example, as shown in FIG. 2, by installing a bypass line 13 between a conduit 1 from a reactor (not shown) and an absorption tower 4, to avoid passing through a waste heat recovery type heat exchanger 4, and by confirming temperature of (meth)acrylic acid-containing gas after confluence, by using a thermometer T, to vary bypassing amount.

Figure 3:
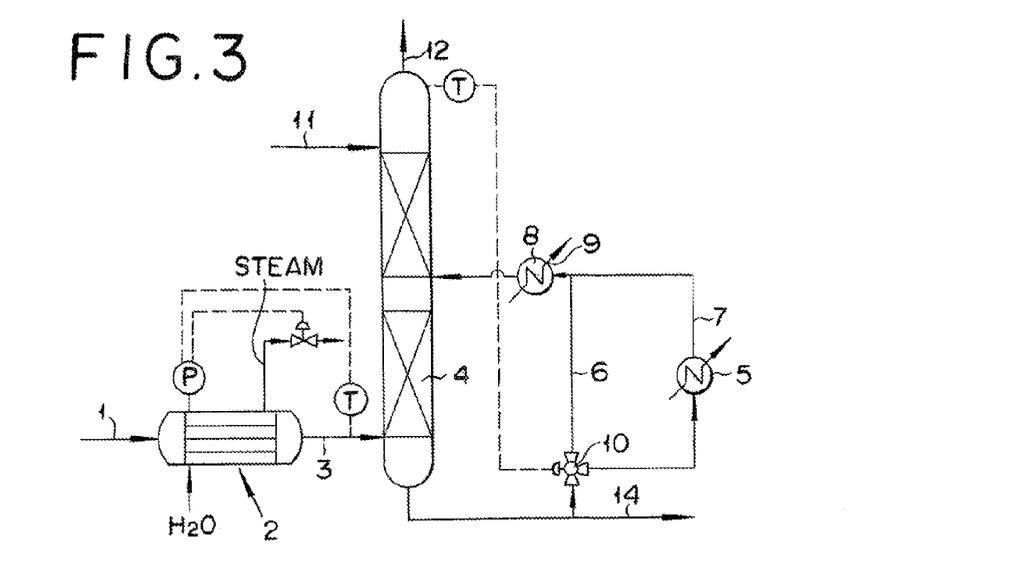
FIG. 3 a flow sheet showing another example of a method for producing (meth)acrylic acid according to the present invention.

(2) A waste heat recovery type heat exchanger 4 for carrying out heat exchange by generation of steam, where temperature of (meth)acrylic acid-containing gas is controlled by varying a steam pressure P (FIG. 3). Variation of the steam pressure can be carried out, for example, as shown in FIG. 3, by confirming temperature of (meth)acrylic acid-containing gas, by using a thermometer T, to vary the pressure.

Figure 4:
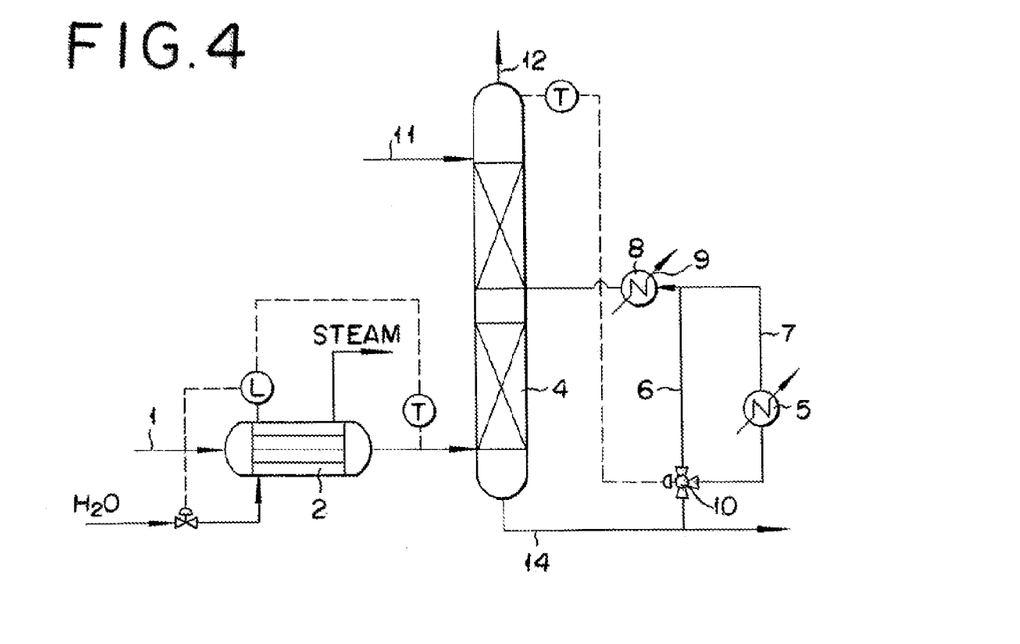
FIG. 4 a flow sheet showing a further other example of a method for producing (meth)acrylic acid according to the present invention.

(3) A waste heat recovery type heat exchanger 4 for carrying out heat exchange by generation of steam, where temperature of (meth)acrylic acid-containing gas is controlled by varying a liquid surface height of liquid inside to be evaporated (FIG. 4). The liquid surface height can be varied by confirming, for example, temperature of (meth)acrylic acid-containing gas, by using a thermometer T, and also by confirming the liquid surface height by using a level indicator L of the liquid surface height.

Figure 5:
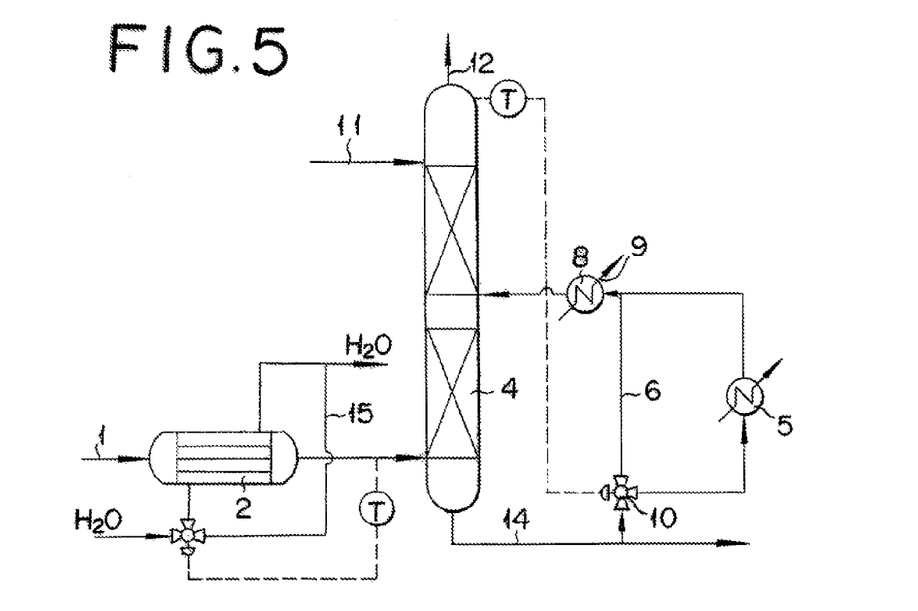
FIG. 5 a flow sheet showing a different example of a method for producing (meth)acrylic acid according to the present invention.

(4) A waste heat recovery type heat exchanger 4 for carrying out heat exchange by passing a cooling medium, where temperature of (meth)acrylic acid-containing gas is controlled by varying a flow amount of the cooling medium (FIG. 5). The flow amount variation of the cooling medium can be carried out, for example, as shown in FIG. 5, by installing a bypass line 15 for a cooling medium, and by confirming temperature of (meth)acrylic acid-containing gas, by using a thermometer T, to vary bypassing amount.

(5) A multiple direct contact type heat exchangers (not shown) for carrying out heat exchange by supplying a cooling medium, where temperature of (meth)acrylic acid-containing gas is controlled by varying number of heat exchangers supplied with the cooling medium. Such temperature control is an embodiment for varying temperature of acrylic acid-containing gas, by installing a plurality of heat exchangers, and by suitable combination of a heat exchanger supplied with the cooling medium, and a heat exchanger not supplied with the cooling medium.

It should be noted that as a cooling medium in the (1) to (5), a conventionally known medium can be used as appropriate, however, for example, water can be used.

It should be noted that the same code through FIGS. 1 to 5 represents the same member.

Explanation will be given in detail below on the present invention, with reference to Examples, however, the present invention should not be limited to the following Examples, and the present invention can be carried out by suitable modifications within a range satisfying a spirit described above and will be described later, and any of such modifications should be included within the technical scope of the present invention.

EXAMPLES

Explanation will be given in detail below on the present invention, with reference to Examples and Comparative Examples.

Comparative Example 1

Figure 1:
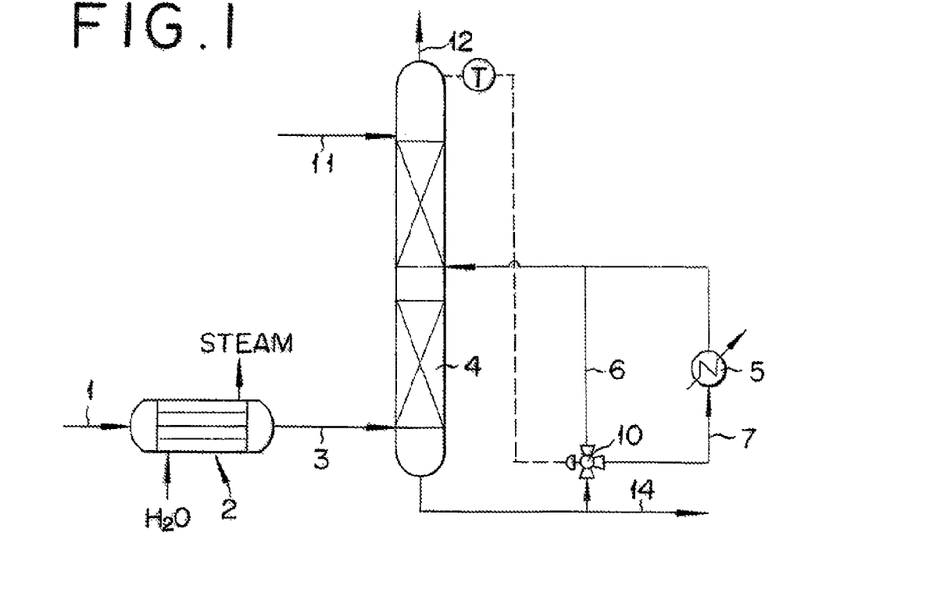
FIG. 1 is a flow sheet showing a conventional method for producing (meth)acrylic acid.

In an apparatus shown in FIG. 1, to a multi-tube type reactor (not shown) for catalytic vapor phase oxidation filled with a catalyst, raw material gas was introduced. By a catalytic vapor phase oxidation reaction, acrylic acid-containing gas, with a composition of 7.1% by volume of acrylic acid, 11.6% by volume of water, 76.5% by volume of nitrogen, 1.5% by volume of oxygen, and 3.3% by volume of other gas, was supplied in a flow rate of 348.5 Nm$^2$/hr to a waste heat recovery boiler 2 via a conduit 1, and gas with a temperature of 280° C. was supplied to the bottom part of an absorption tower 4 via a conduit 3.

As an absorbing agent, 45 kg/hr of water was supplied from the upper part of the absorption tower 4 via a conduit 11, and pressure at the tower top part of the absorption tower 4 was set to be 11 kPa (gauge pressure), and temperature at the tower top was set to be 68° C. by detecting with a thermometer T to carry out absorption of acrylic acid, and non-condensable gas containing 25.4% by volume of water was taken out in a flow rate of 379.0 Nm$^3$/hr, from the tower top part via a conduit 12. In addition, a part of an acrylic acid solution (temperature: 95° C.) obtained from the tower bottom part of the absorption tower 4 was subjected to heat removal by a cooler 5 present at a circulation line 7, and a part of the acrylic acid solution was circulated to the lower part of the absorption tower 4, and by adjusting amount passing through the cooler 5 by installing a bypass line 6 not passing through the cooler 5, cooling (heat removal) of the absorbing solution in the absorption tower 4 was controlled, to try control of concentration of acrylic acid in an acrylic acid solution.

In the case where temperature of acrylic acid-containing gas, supplied to the absorption tower, is set to be 280° C., assuming the case of deterioration of a catalyst in practical operation, it was required that heat removal amount in the absorption tower 4 to set to be 8600 kcal/hr. Therefore, heat removal was carried out by passing 0.22 m$^3$/hr of 1.0 m$^3$/hr of a circulating aqueous solution of acrylic acid through the cooler 5, so that the above heat removal amount was secured. In this case, by setting ratio between amount of an aqueous solution of acrylic acid, passing through the cooler 5, and amount of an aqueous solution of acrylic acid, bypassing, to be 1:3.5, that is within controllable operation range by a control valve 10, control to the objective heat removal amount can be attained. As a result, condensation of an aqueous solution of acrylic acid from acrylic acid-containing gas, and separation of non-condensable gas could be carried out stably, and an aqueous solution of acrylic acid having a high acrylic acid concentration of 91% by mass could be obtained from a conduit 14.

On the other hand, in the case where temperature of acrylic acid-containing gas to be supplied to the absorption tower is set to be 230° C., assuming the case of no deterioration of a catalyst during practical operation, it was required that heat removal amount in the absorption tower to set to be 1800 kcal/hr, as calculated value, to make temperature at the tower top of the absorption tower 4 nearly the same as temperature in the above case, and to make concentration of an acrylic acid solution to nearly the same. To attain such a heat removal amount, it was necessary that amount of an aqueous solution of acrylic acid, passing through the cooler 5, should be furthermore reduced as compared with the above case. Therefore, reduction of amount passing through the cooler was tried, however, control to objective flow amount could not be attained within an operational range of the control valve 10, and thus objective heat removal amount could not be attained. As a result, heat removal amount fluctuated, and temperature at the tower top part of the absorption tower 4 fluctuated in a range of ±1° C., with this fluctuation. As a result, condensation amount of acrylic acid, and water amount taken out accompanied with non-condensable gas from the tower top part fluctuated, and concentration of acrylic acid, obtained from the tower bottom of the absorption tower 4, fluctuated in a range of from 87 to 94%. Therefore, the reaction and capturing were forced to stop.

Example 1

In an apparatus shown in FIG. 2, similarly as in Comparative Example 1, a reaction and cooling by a waste heat recovery type heat exchanger 2 were carried out, and a cooling circulation line 7 and a bypass line 6 were arranged at the absorption tower 4, and also a heat exchanger 8 that is capable of heating the cooling circulation line 7 was installed.

In the case where temperature of acrylic acid-containing gas, sent to the absorption tower 4, was 230° C., by flowing steam having a pressure of 0.2 MPaG to a heat exchanger 8 for heating via a conduit 9, heating in a rate of 4200 kcal/hr was carried out, along with heat removal in a rate of 6000 kcal/hr was carried out by a cooler 5. By detecting temperature at the tower top (68° C.) by using a thermometer T, and by setting ratio between amount of an aqueous solution of acrylic acid, circulating the cooler 5, and amount of an aqueous solution of acrylic acid bypassing to be 1:5.6, which was an operation range controllable by a control valve 10, control to the objective heat removal amount (1800 kcal/hr) could be attained. As a result, condensation of an aqueous solution of acrylic acid from acrylic acid-containing gas, and separation of non-condensable gas could be stably carried out, and an aqueous solution of acrylic acid having an acrylic acid concentration of 91% by mass could be stably obtained from a conduit 14.

Conditions in each of Comparative Example 1 and Example 1 are shown in Table 1.

Examples 2 to 4

Tests were carried out by changing temperature of supplying gas to the absorption tower 4 to 240° C., 250° C., and 260° C., in a similar method as in Example 1, and results shown in Table 1 were obtained.

TABLE 1

|  | Comp. Example 1 | | Example 1 | | | |
| --- | --- | --- | --- | --- | --- | --- |
|  | Last stage catalyst | Initial stage | Initial stage catalyst | Example 2 | Example 3 | Example 4 |
| Gas temperature to be supplied to absorption tower degree C. | 280 | 230 | 230 | 240 | 250 | 260 |
| Required heat removal amount at absorption tower kcal/hr | 8600 | 1800 | 1800 | 3200 | 4500 | 5900 |
| Heating amount at absorption tower bottom kcal/hr | 0 | 0 | 4200 | 2800 | 0 | 0 |
| Totally required heat removal amount kcal/hr | 8600 | 1800 | 6000 | 6000 | 4500 | 5900 |
| Circulation amount to absorption tower bottom m$^3$/hr | 1 | 1 | 1 | 1 | 1 | 1 |
| Amount passing cooler in above amount m$^3$/hr | 0.22 | 0.05 | 0.15 | 0.15 | 0.11 | 0.15 |
| Bypass amount:amount passing cooler | 1:3.5 | 1:19 | 1:5.6 | 1:5.6 | 1:7.7 | 1:5.7 |
| Bypass ratio % | 22 | 5 | 15 | 15 | 11 | 15 |
| Control Valve control | Possible | Impossible | Possible | Possible | Possible | Possible |
| Concentration of aq. solution of acrylic acid %* | 91 | 87-94 | 91 | 91 | 91 | 91 |

(Note);
Comp Example: Comparative Example
*Concentration of an. aqueous solution of acrylic acid (% by mass)
Controllable range of control valve: 10 to 90%

Comparative Example 2

In an apparatus shown in FIG. 1, to a multi-tube type reactor for catalytic vapor phase oxidation (not shown) filled with a catalyst, raw material gas was introduced in a flow rate of 360.3 Nm$^3$/hr. By a catalytic vapor phase oxidation reaction, acrylic acid-containing gas, with a composition of 7.1% by volume of acrylic acid, 11.6% by volume of water, 76.5% by volume of nitrogen, 1.5% by volume of oxygen, and 3.3% by volume of other gas was obtained.

Temperature of gas discharged from the reactor was 350° C., and this gas was introduced in a flow rate of 348.5 Nm$^3$/hr to a waste heat recovery type heat exchanger 2, which is capable of carrying out heat removal by generation of steam, via a conduit 1. Pressure of the generated steam of the heat exchanger 2 was 0.7 MPaG, and by passing the gas through the heat exchanger 2, acrylic acid-containing gas was cooled to 250° C. This acrylic acid-containing gas was supplied from the lower part of the absorption tower 4, and by using 45 kg/hr of water, as an absorbing agent, an aqueous solution of acrylic acid was captured through a conduit 11, and non-condensable gas was separated via a conduit 12 from the tower top. As a result, temperature control of a capturing tower for making high concentration can be stably carried out by a cooler at the tower bottom, and an aqueous solution of acrylic acid having a concentration of 91% could be stably obtained.

After that, a reaction was stopped to exchange a reaction catalyst. In addition, the heat exchanger 2 was washed during the catalyst exchange. After completion of the catalyst exchange, a reaction was started again under the same reaction condition to obtain acrylic acid-containing gas with a temperature of 250° C. from the reactor. The gas was introduced to the waste heat recovery type heat exchanger 2 at a flow rate of 348.5 Nm$^3$/hr, and the acrylic acid-containing gas was found to be cooled at 188° C. after passing through the heat exchanger. Then, under the same condition as above, an aqueous solution of acrylic acid was captured, and it was found that temperature at the tower top of the absorption tower 4 was lowered, and condensation of substances with lower boiling point than that of acrylic acid increased. In addition, temperature control of the tower bottom of the absorption tower 4, by the cooler became difficult, resulting in lowering of concentration of acrylic acid down to 71 to 72%, and a high concentration aqueous solution of acrylic acid did not become obtainable, and thus the operation was forced to stop.

Example 5

In an apparatus shown in FIG. 2, under similar condition as in Comparative Example 2, a reaction was carried out after catalyst exchange to obtain acrylic acid-containing gas of 250° C. by a reactor (not shown). As shown by the Figure, as for this gas, only 87.3 Nm$^3$/hr of acrylic acid-containing gas was introduced to a waste heat recovery type heat exchanger 5, without passing a part of acrylic acid-containing gas through the waste heat recovery type heat exchanger 2 by using a bypass line 13. By being passed through the heat exchanger 5, acrylic acid-containing gas was cooled to 170° C., and after confluence with acrylic acid-containing gas that passed through the bypass line 13 in a flow rate of 261.2 Nm$^3$/hr, temperature of acrylic acid-containing gas became 230° C.

Acrylic acid was captured from the converging gas under the same condition as in the above Comparative Example, and thus temperature to obtain a high concentration acrylic acid solution could be stably controlled by a cooler 5 at the tower bottom of the absorption tower 4, and an aqueous solution of acrylic acid having a concentration of 91% by mass could be stably obtained. In this way, by adjusting temperature of acrylic acid-containing gas, supplied to the absorption tower 4, by means of adjusting amount of acrylic acid-containing gas, to be introduced to the waste heat recovery type heat exchanger 2, in response to temperature of acrylic acid-containing gas, obtained by a reactor, concentration of the resulting solution of acrylic acid could be made nearly the same as in the case where temperature of gas discharged from a reactor was 350° C., and thus the absorption tower 4 could be stably operated.

Example 6

In an apparatus shown in FIG. 3, under similar condition as in Comparative Example 2, a reaction was carried out after catalyst exchange to obtain acrylic acid-containing gas of 250° C. by a reactor (not shown). As shown in the Figure, by using a waste heat recovery type heat exchanger 2, which is capable of varying pressure of steam generating, pressure of steam generating was set to be 2.5 MPa. Acrylic acid-containing gas was introduced to this heat exchanger 2, and found to be cooled to 230° C. This gas was subjected to capturing in an aqueous solution of acrylic acid under the same condition as in the Comparative Example 2, and thus temperature to obtain a high concentration acrylic acid solution could be stably controlled by a cooler 5 at the tower bottom of the absorption tower 4, and an aqueous solution of acrylic acid having a concentration of 91% by mass could be stably obtained. In this way, by adjusting pressure of steam generating from the waste heat recovery type heat exchanger 2, in response to temperature of acrylic acid-containing gas, obtained by a reactor, so that temperature of acrylic acid-containing gas, supplied to the absorption tower, is made nearly the same as in the case where temperature of gas discharged from a reactor was 350° C., the absorption tower 4 could be stably operated.

Example 7

In an apparatus shown in FIG. 4, under similar condition as in Comparative Example 2, a reaction was carried out after catalyst exchange to obtain acrylic acid-containing gas of 250° C. by a reactor (not shown). This gas was cooled by using the same waste heat recovery type heat exchanger 2 as in Comparative Example 2. However, this gas was introduced by adjusting liquid surface height of boiler water inside the heat exchanger as shown by the Figure, so that heat transferable area becomes 19% based on that in Comparative Example 2, and it was found to be cooled to 230° C. This gas was subjected to absorption in an aqueous solution of acrylic acid under the same condition as in the Comparative Example 2, and temperature to obtain a high concentration acrylic acid solution could be stably controlled by a cooler 5 at the tower bottom of the absorption tower 4, and an aqueous solution of acrylic acid having a concentration of 91% by mass could be stably obtained. In this way, by varying liquid surface height in the boiler of a waste heat recovery type heat exchanger (not shown), in response to temperature of acrylic acid-containing gas, obtained by a reactor, temperature of acrylic acid-containing gas, supplied to the absorption tower, could be made nearly the same as in the case where temperature of gas discharged from a reactor was 350° C., and the absorption tower could be stably operated.

Example 8

In an apparatus shown in FIG. 5, under similar condition as in Comparative Example 2, a reaction was carried out after catalyst exchange to obtain acrylic acid-containing gas of 250° C. by a reactor 2. As shown in this Figure, as a cooling medium, a waste heat recovery type heat exchanger 2, which passes water to be supplied to a boiler at a temperature of 105° C., was used, and a bypass 15 was installed at a supply line of water to be supplied to a boiler, to set amount of water to be supplied to a boiler passing the waste heat recovery type heat exchanger 2 to be 0.6 m$^3$/hr. By introducing acrylic acid-containing gas, to the heat exchanger 2, under the same condition as in Comparative Example 2, acrylic acid-containing gas was cooled to 230° C. This gas was subjected to absorption in an aqueous solution of acrylic acid under the same condition as in the Comparative Example 2, and temperature to obtain a high concentration acrylic acid solution could be stably controlled by a cooler 5 at the tower bottom of the absorption tower 4, and an aqueous solution of acrylic acid having a concentration of 91% by mass could be stably obtained. Note that temperature of water to be supplied to a boiler, discharged from the heat exchanger 2, was 140° C., and temperature thereof after confluence with bypassed water to be supplied to a boiler was 120° C. In this way, by adjusting amount of water to be supplied to a boiler, which is supplied to the waste heat recovery type heat exchanger 2, in response to temperature of acrylic acid-containing gas, obtained by a reactor, temperature of acrylic acid-containing gas, supplied to the absorption tower, could be made nearly the same as in the case where temperature of gas discharged from a reactor was 350° C., and the capturing tower could be stably operated.

Conditions in each of Comparative Example 2 and Examples 1 to 4 are shown in Table 2.

TABLE 2

| | Comp. Example 2 | Example 5 | Example 6 | Example 7 | Example 8 |
|---|---|---|---|---|---|---|
| | Last stage | Initial stage | Initial stage | Initial stage | Initial stage | Initial stage |
| Reaction gas degree C. | 350 | 250 | 250 | 250 | 250 | 250 |
| Gas temp. to be supplied to absorption tower degree C. | 250 | 188 | 230 | 230 | 230 | 230 |
| Steam pressure generating at waste heat recovery Mpa | 0.7 | 0.7 | 0.7 | 2.5 | 0.7 | — |
| Amount passing waste heat recovery NM$^3$/hr | 348.5 | 348.5 | 87.3 | 348.5 | 348.5 | 348.5 |
| Reaction gas bypass amount NM$^3$/hr | — | — | 261.2 | — | — | — |
| Temp. at exit of waste heat recovery degree C. | — | — | 170 | — | — | — |
| Effective heat conduction area of waste heat recovery m$^2$ (Liquid level adjustment) | 100% | 100% | 100% | 100% | 19% | 100% |
| Cooling water amount m$^3$/hr | — | — | — | — | — | 0.6 |
| Cooling water bypass amount *1 m$^3$/hr | — | — | — | — | — | 0.9 |

TABLE 2-continued

|  | Comp. Example 2 | Example 5 | Example 6 | Example 7 | Example 8 |
|---|---|---|---|---|---|
|  | Last stage | Initial stage | Initial stage | Initial stage | Initial stage | Initial stage |
| Concentration of aq. solution of acrylic acid %* | 91 | 71-72 | 91 | 91 | 91 | 91 |

*Concentration of aq. solution of acrylic acid (% by mass)
At 230 C. degree, it was required to heat the bottom part of an absorption tower to make control using CV possible As shown in the above Examples, according to the present invention, by making temperature of gas supplied inside a separation apparatus of non-condensable gas nearly constant, regardless of fluctuation of temperature of (meth)acrylic acid-containing gas, discharged from a reactor, temperature control of an absorption tower to obtain a high concentration solution became possible by a cooler installed at the absorption tower, and as well suppression of fluctuation of concentration of an aqueous solution of acrylic acid, obtained from the tower bottom of the absorption tower, became possible. As a result, the absorption step of acrylic acid could be stably operated. In addition, by setting temperature of acrylic acid-containing gas, supplied to the absorption tower, to be equal to or higher than 200° C., a high concentration aqueous solution of acrylic acid having a concentration of equal to or higher than 90% by mass could be obtained.

INDUSTRIAL APPLICABILITY

According to the present invention, a high concentration acrylic acid solution can be stably obtained, regardless of fluctuation of temperature of (meth)acrylic acid-containing gas, obtained by a catalytic vapor phase oxidation reaction. Therefore, a method for producing acrylic acid, using the present invention, enables to largely reduce load and work in the steps subsequent to the separation step of non-condensable gas, and further more enhance production efficiency as compared with a conventional method.

The invention claimed is:

1. A method for producing (meth)acrylic acid comprising:
    (1) subjecting a raw material of (meth)acrylic acid to catalytic vapor phase oxidation by molecular oxygen-containing gas, in the presence of an oxidation catalyst to produce (meth)acrylic acid-containing gas;
    (2) cooling said (meth)acrylic acid-containing gas; and
    (3) obtaining a (meth)acrylic acid solution by introducing said cooled gas to an absorption tower and contacting said cooled gas with an absorbing agent for acrylic acid to separate non-condensable gas,
    characterized in that a (meth)acrylic acid solution with a high concentration of equal to or higher than 75% by mass is obtained, by setting a lower temperature limit not less than 200° C. in step (2) for cooling said (meth)acrylic acid-containing gas, from the operation conditions for step (3), and controlling the cooling of said gas during whole reaction period so that said gas temperature does not become below said lower limit of cooling temperature.

2. The method according to claim 1, wherein said temperature control is carried out by controlling the amount of heat removed from the (meth)acrylic acid-containing gas introduced to the absorption tower, in response to the temperature of the (meth)acrylic acid-containing gas produced by said catalytic vapor phase oxidation reaction.

3. The method according to claim 2, wherein a gas temperature control means is installed between the catalytic vapor phase oxidation reaction and the absorption tower.

4. The method according to claim 1, wherein the temperature of the (meth)acrylic acid-containing gas supplied to said absorption tower is controlled from 200 to 300° C.

5. The method according to claim 4, wherein the temperature of the (meth)acrylic acid-containing gas supplied to said absorption tower is controlled from 210 to 290° C.

6. The method according to claim 5, wherein the temperature of the (meth)acrylic acid-containing gas supplied to said absorption tower is controlled from 230 to 280° C.

7. The method according to claim 1, wherein the temperature fluctuation range of the (meth)acrylic acid-containing gas supplied to said absorption tower is controlled within 30° C.

8. The method according to claim 1, wherein the fluctuation range between maximal value and minimal value of concentration of (meth)acrylic acid in the (meth)acrylic acid solution taken out from the tower bottom of said absorption tower is ±2%.

9. The method according to claim 1, wherein the water concentration of the (meth)acrylic acid solution discharged from said absorption tower is set from 1 to 10% by mass.

10. The method for producing (meth)acrylic acid according to claim 1, wherein the gas temperature control means is a waste heat recovery type heat exchanger for carrying out heat exchange by generation of steam, where the temperature of (meth)acrylic acid-containing gas is controlled by varying the pressure of steam.

11. The method for producing (meth)acrylic acid according to claim 1, wherein a (meth)acrylic acid solution with a concentration of equal to or higher than 75% by mass is obtained, by controlling temperature of the tower bottom solution of said absorption tower through heating or cooling, re-circulating said bottom solution to said absorption tower, and repeating step (3), wherein said heating or cooling is carried out by a control means provided in the acrylic acid absorption tower.

12. The method for producing (meth)acrylic acid according to claim 1, wherein the gas temperature control means is a waste heat recovery type heat exchanger where the temperature of (meth)acrylic acid-containing gas is controlled by varying the supply amount of (meth)acrylic acid-containing gas passing through inside.

13. The method for producing (meth)acrylic acid according to claim 1, wherein the gas temperature control means is a waste heat recovery type heat exchanger for carrying out heat exchange by generation of steam, where the temperature of (meth)acrylic acid-containing gas is controlled by varying the liquid surface level of liquid inside to be evaporated.

14. The method for producing (meth)acrylic acid according to claim 1, wherein the gas temperature control means is a waste heat recovery type heat exchanger for carrying out heat exchange by passing a cooling medium, where the temperature of (meth)acrylic acid-containing gas is controlled by varying the flow rate of the cooling medium.

15. The method for producing (meth)acrylic acid according to claim 1, wherein the temperature fluctuation range of the (meth)acrylic acid-containing gas supplied to said absorption tower is controlled within 40° C.

* * * * *